United States Patent
Chang

(12) 
(10) Patent No.: US 7,259,153 B2
(45) Date of Patent: Aug. 21, 2007

(54) DRUG FORMULATION AND DELIVERY USING CRYSTALLINE METHYLATED CYCLODEXTRINS

(75) Inventor: Rong-Kun Chang, Rockville, MD (US)

(73) Assignee: Supernus Pharmaceuticals, Rockville, MD (US)

( * ) Notice: Subject to any disclaimer, the term of this patent is extended or adjusted under 35 U.S.C. 154(b) by 470 days.

(21) Appl. No.: 10/770,727

(22) Filed: Feb. 2, 2004

(65) Prior Publication Data

US 2004/0157797 A1    Aug. 12, 2004

Related U.S. Application Data

(60) Provisional application No. 60/444,455, filed on Feb. 3, 2003.

(51) Int. Cl.
*A01N 43/04* (2006.01)
*A61K 31/715* (2006.01)
*C08B 37/16* (2006.01)

(52) U.S. Cl. .............................. 514/58; 514/54; 536/46; 536/102; 536/103

(58) Field of Classification Search ................... 536/46, 536/102, 103; 514/54, 58
See application file for complete search history.

(56) References Cited

U.S. PATENT DOCUMENTS

| 5,472,954 | A | * | 12/1995 | Loftsson | ....................... 514/58 |
| 5,681,828 | A | | 10/1997 | Pitha | |
| 5,935,941 | A | | 8/1999 | Pitha | |
| 6,110,498 | A | | 8/2000 | Rudnic et al. | |
| 6,284,276 | B1 | | 9/2001 | Rudnic et al. | |
| 6,464,988 | B1 | * | 10/2002 | Gidwani et al. | ............. 424/400 |
| 6,828,334 | B2 | * | 12/2004 | Gidwani et al. | ............ 514/338 |

* cited by examiner

*Primary Examiner*—Patrick Lewis
(74) *Attorney, Agent, or Firm*—Patricia Granados; Anna Ganelina

(57) ABSTRACT

The present invention is directed to pharmaceutical compositions containing crystalline methylated cyclodextrins, which enhance the solubility of the pharmaceutically active agent or agents of the formulation.

10 Claims, No Drawings

DRUG FORMULATION AND DELIVERY USING CRYSTALLINE METHYLATED CYCLODEXTRINS

This nonprovisional application claims the benefit of U.S. Provisional Application No. 60/444,455 filed Feb. 3, 2003, the entirety of which is incorporated herein by reference.

FIELD OF THE INVENTION

The present invention is directed to pharmaceutical compositions containing crystalline methylated cyclodextrins, which enhance the solubility of the pharmaceutically active agent of the formulation.

BACKGROUND OF THE INVENTION

Among drug candidates under evaluation/development, the problem of inadequate aqueous solubility is likely to be encountered with relatively high frequency. Inadequate aqueous solubility is a significant hurdle in formulating such compounds into a simple, isotonic, ready-to-inject aqueous solution. For oral administration, poor aqueous solubility of drugs can jeopardize the dissolution rate and bioavailability. Inadequate aqueous solubility reflects a less than desirable free energy of transfer from the solid phase to the aqueous solution. This may result from two causes: (a) polar compounds may exhibit low water solubility as a result of strong crystalline interaction due to intermolecular electrostatic attraction and/or hydrogen bonding in the crystal; or (b) lipophilic/hydrophobic compounds are likely to exhibit low water solubility due to unfavorable free energy of salvation by water. No matter the cause of the solubility problem, cyclodextrin complexation, micellar solubilization, cosolvency, and solutropy are four strategies that are commonly employed in circumventing the problem.

However, in general, a disadvantage of micellar solubilization is the large quantity of surfactant required to provide the several orders of magnitude increases in solubility often desired. In addition, surfactant toxicity at high concentrations, particularly hemolysis, is a well-documented problem. The rapid reversibility of solubilization is another difficulty in the use of micellar solution as an approach for parenteral or oral route.

Oftentimes, non-aqueous solvents can effectively dissolve the drugs with inadequate aqueous solubility. For example, carbamazepine solubility in propylene glycol is about 310 fold of carbamazepine aqueous solubility. However, the toxicity of the non-aqueous solvents is a major concern. A 40% propylene glycol/water cosolvent system is near the upper limit in terms of its organic solvent composition for physiological compatibility. Based on metabolic and toxicological data, the WHO has set an acceptable daily intake of propylene glycol at up to 25 mg/kg body weight. Additionally, the solubility enhancement generally is significantly reduced in the mixture of non-aqueous solvent and water, compared to non-aqueous solvent alone.

The term "solutropy" was introduced to describe solubilization by the addition of a large amount of a second solute in both aqueous and nonaqueous solvents. The solubility enhancement either via solvent structure modification or via chemical complexation has been demonstrated in pharmaceutical applications. The following are the examples of hydrotropes commonly used in the pharmaceutical industry: nicotinamide, sodium salts of benzoic, naphtholic, and nicotinic acids, urea, sorbitol, fructose, sodium salicylate, sodium glycinate, and gentisate sodium. Toxicity of these hydrotropes, however, is a major concern. Furthermore, the solubility enhancement is compound-dependent and only modest enhancement can be expected using the hydrotrope approach.

Pharmaceutical applications of cyclodextrins have been considered for over 30 years. Cyclodextrins are cyclic oligosaccharides composed of 6-8 dextrose units ($\alpha$-, $\beta$-, and $\gamma$-cyclodextrins, respectively) joined through 1-4 bonds. Because the interior of these molecules are relatively lipophilic and the exterior relatively hydrophilic, they tend to form inclusion complexes.

Safety is a major issue with any new material. Two of the parent cyclodextrins, i.e., $\alpha$- and $\beta$-cyclodextrins, are known to be parenterally unsafe due to severe nephrotoxicity. However, $\alpha$- and $\beta$-cyclodextrins have been used orally in both food products and in various approved pharmaceuticals. Other than the safety issue, low aqueous solubility is another drawback to using the parent cyclodextrins, which is especially true for $\beta$-cyclodextrin; the ring cavity for $\alpha$-cyclodextrin is simply too small to encapsulate the drug molecules, in most cases.

Modification of the parent cyclodextrins to improve safety while maintaining the ability to form inclusion complexes with various substrates has been the goal of numerous research groups. The most significant cyclodextrin derivatives are the following: hydroxypropyl $\beta$-cyclodextrin, glucuronylglucosyl $\beta$-cyclodextrin, sulfobutylether $\beta$-cyclodextrin, and methylated $\beta$-cyclodextrin. These modified cyclodextrins and parent cyclodextrins provide have assisted formulators in overcoming solubility problems of poorly water-soluble drugs in various applications, i.e., parenteral, oral, buccal, ophthalmic, nasal, dermal, rectal, and pulmonary routes. While several cyclodextrins have been approved for use in pharmaceutical products, such as Sporanox (Janssen), Zeldox/Geodon (Pfizer), and Vfend (Pfizer), there is a need to find additional cyclodextrins to contribute to the formulators' arsenal. Although cyclodextrins are not the solution to all the solubility problems, they definitely have higher potential than other solubilization techniques.

DETAILED DESCRIPTION OF THE INVENTION

The present invention is directed to cyclodextrin derivatives that, it has now been found, are useful in pharmaceutical applications, and act as solubilizing agents. These cyclodextrin derivatives are crystalline methylated cyclodextrins, more specifically, crystalline methylated $\alpha$-, $\beta$-, and/or $\gamma$-cyclodextrins. Preferably, the cyclodextrin is crystalline methylated $\gamma$-cyclodextrin. Generally, the compounds may be produced by methylating a mole of $\alpha$-, $\beta$-, and/or $\gamma$-cyclodextrin with 3-6 moles of dimethyl sulfate in water using calcium hydroxide as a base (i.e., base of minimal effective basicity). Crystals start to separate from concentrated solutions of the methylated $\alpha$-, $\beta$-, and/or $\gamma$-cyclodextrins. The yield of crystals in such reactions is between 30 to 70%. Additionally, any of the methods disclosed in U.S. Pat. Nos. 5,681,828 and 5,935,941 can be used to produce the cyclodextrin derivatives usable in the compositions of the present invention, and each of these patents in their entireties are incorporated herein by reference.

In one aspect of the invention is crystalline methylated β-cyclodextrin, which is stable against heat and humidity. This crystalline cyclodextrin derivative has good water solubility, and at room temperature preparations with solubility around 15% can easily be made. In addition, crystalline methylated β-cyclodextrin has much better solubilization efficacy than other commercially available cyclodextrins and cyclodextrin derivatives. Additionally, the parent compound, β-cyclodextrin, is less expensive than gamma-cyclodextrin, which makes it more desirable. Methods of making this compound are disclosed in the '828 and '941 patents, supra, for instance Example 11 of both patents teaches such a method.

More specifically, the invention is directed to pharmaceutical compositions containing the crystalline methylated α-, β-, and/or γ-cyclodextrins and a pharmaceutically active agent. As preferred embodiments are compositions containing crystalline methylated β-cyclodextrin. For all practical purposes, the active agent is one that has proven difficult to solubilize in aqueous solutions, although the invention is not necessarily limited thereto. In other words, the active agent is one that is poorly soluble in aqueous solutions, it being understood that "poorly soluble" is generally meant to denote an agent that has low aqueous solubility. Poorly soluble can be defined here as one part of solute required more than 100 parts of solvent to dissolve the solute.

The compositions may contain any one of the cyclodextrin derivatives or may have any combination of mixtures thereof. In a preferred embodiment, the cyclodextrin is only crystalline methylated β-cyclodextrin.

The compositions are not limited to containing only one active agent; there may be more than one agent. For instance, there may be one agent with low solubility and one without, or two agents with low solubility, etc. Further, "pharmaceutically active agent" is intended to include, other than therapeutic drugs, diagnostic and nutritional agents.

The compositions are generally in a solid form or liquid form. Typically, they are in dosage unit form, such as tablet, powder, sachet, bead, pellet, osmotic dosage form, etc., but they may as well be in a liquid, cream or aerosol form for use in various applications, i.e., parenteral, oral, buccal, ophthalmic, nasal, dermal, rectal, and pulmonary routes. Preferably, for patient convenience, the compositions are in an oral delivery form, such as a tablet, capsule or osmotic dosage form, for example. Most preferably, however, the compositions are in an osmotic dosage form, several of which are described inter alia in U.S. Pat. No. 6,110,498, and 6,284,276, which are incorporated in their entireties herein by reference.

Additional pharmaceutically acceptable carriers or excipients may be present in the compositions as desired, these additional substances having essentially no substantial affect on the solubility performance that is key to the present invention. Such excipients/carriers are well known in the art, and are described in Gennaro et al., Remington's Pharmaceutical Sciences (18th ed., Mack Publishing Company, 1990, see especially Part 8: Pharmaceutical Preparations and their Manufacture), which is in its entirety incorporated herein by reference.

The compositions of the present invention can be formulated and used in various applications, i.e., parenteral, oral, buccal, ophthalmic, nasal, dermal, rectal, and pulmonary routes.

The present invention is demonstrated in the following examples, it being understood that these are for illustrative purposes only, and the invention is not intended to be limited thereto.

EXAMPLE

Materials and Methods

Materials

A crystalline methylated β-cyclodextrin, molecular weight 1200 amu, was supplied by Pitha & Pitha. Hydroxypropyl β-cyclodextrin, β-cyclodextrin, and γ-cyclodextrin were received as a gift from Cerestar. Methylated β-cyclodextrin (amorphous) was a gift from Wacker-Chemie. Glucuronylglucosyl-β-cyclodextrin was purchased from Wako Pure Chemical Industries, Ltd.

Methods

An excess of drug substance was added to 20 ml glass liquid scintillation vials (Kimble Glass Inc., Vineland, N.J.) containing 10 ml of the media with a specific amount of solubilizer. The sample vials were then rotated using an end-over-end mechanical rotator at 50 rpm at room temperature for 48 hours to reach equilibrium solubility. The samples were filtered through a 0.45 μm filter (Acrodisc CR PTFE membrane filter, Gelman Sciences, Ann Arbor, Mich.). After discarding the first mL of the filtrates to eliminate any membrane adsorptive effect, the filtrates were collected for high-performance liquid chromatography (HPLC) analysis for drug concentration.

Results and Discussion

While the use of α-, β-, or γ-cyclodextrin as complexing agents would be considered a classical approach, recently developed chemically modified α-, β-, and γ-cyclodextrins, particularly the crystalline methylated β-cyclodextrins, represent a novel class of solubilizing agents with improved water solubility, solubilization potency, and safety profile. Table 1 shows the solubilization potency of the crystalline methylated β-cyclodextrin with carbamazepine compared to three commercially available cyclodextrins. When compared on a weight basis, the crystalline methylated β-cyclodextrin clearly outperforms other cyclodextrins. It may be noted that the parent β-cyclodextrin suffers a significant drawback of low aqueous solubility (i.e., 1.8% w/v). Micellar solubilization is another commonly used approach to improve solubility of poorly-water soluble drugs. However, in general, a disadvantage of micellar solubilization is the large quantity of surfactant required to provide the several orders of magnitude increases in solubility often desired. In addition, surfactant toxicity at high concentrations, particularly hemolysis, is a well-documented problem. The rapid reversibility of solubilization is another difficulty in the use of micellar solution as an approach for parenteral or oral route. Oftentimes, nonaqueous solvents can effectively dissolve the drugs with inadequate aqueous solubility. For example, carbamazepine solubility in propylene glycol is about 310 fold of carbamazepine aqueous solubility (Table 2). However, the toxicity of the non-aqueous solvents is a major concern. A 40% propylene glycol/water cosolvent system is near the upper limit in terms of its organic solvent composition for physiological compatibility. Based on metabolic and toxicological data, the WHO has set an acceptable daily intake of propylene glycol at up to 25 mg/kg body weight.

Table 3 shows the solubilization potency of crystalline methylated β-cyclodextrin with fenofibrate, compared to hydroxypropyl β-cyclodextrin. The crystalline methylated β-cyclodextrin outperforms hydroxypropyl β-cyclodextrin in the aqueous system.

In the oxcarbazepine case, crystalline methylated β-cyclodextrin behaves much better than other cyclodextrins tested in terms of solubilization potency (Table 4). Again, in the glipizide case, crystalline methylated β-cyclodextrin outperforms other commercially available cyclodextrins in terms of solubilization potency, in contrast to no solubility enhancing for γ-cyclodextrin (Table 5).

CONCLUSIONS

Consistently, crystalline methylated β-cyclodextrin provides superior solubilization efficiency for four model compounds, compared to other parent cyclodextrins and derivatives. Additionally, cyclodextrins are capable of enhancing the solubility of drugs in non-aqueous polar vehicles.

Other than the direct use of methylated cyclodextrins as solubilizer in a liquid form (i.e., injectable solution, Liquid filled capsule, oral suspension, oral syrup), dried inclusion complexes of the present invention can be prepared by mixing the methylated cyclodextrin with the water-insoluble or slightly water-soluble compound according to known methods, such as the coprecipitation method (Crassons, et al., 5$^{th}$ Int. Conf. Pharmaceutical Technology, Paris, May 30 to Jun. 1, 1989, incorporated herein by reference), lyophilization or spray drying method (Kurozumi et al., Chem. Pharm. Bull., 23, 3062 (1975); Kata et al., Pharmazie, 39, 856 (1984), each of which is incorporated herein by reference), and milling/kneading/granulating method (J. Szejtli et al., "Cyclodextrins and their inclusion complexes", Akadecimial Kiado, Budapest (1982), p. 109-114; Kyowa Jap. Prov. Pat. Pubin. No. 106698 (1982), each of which is incorporated herein by reference.

The inclusion compounds prepared can be incorporated into various dosage forms. The dosage forms include, but are not limited to, the following: capsule, tablet, powder, beads, ointment, and lotion. In addition, the cyclodextrin derivatives of the invention can act as solubilizing agents in sustained-release dosage form. Especially for osmotic pumps, the present cyclodextrin derivatives can also function as osmotic agents providing the influx of water and osmotic pressure to push the drug molecule out of such systems.

TABLE 1

Solubility of Carbamazepine in Aqueous Solution of Various Cyclodextrins

| Concentration. % (w/v) | β-Cyclodextrin[2] | Cavasol W7M[3] | Cryst. Methylated β-CD[4] | HP-β-cyclodextrin |
|---|---|---|---|---|
| | Carbamazepine Solubility, mg/ml (solubility enhancement ratio)[1] | | | |
| 0 | 0.113 | 0.113 | 0.113 | 0.113 |
| 1 | 0.669 (5.9) | — | — | — |
| 2 | 1.186 (10.5) | 1.068 (9.5) | 1.542 (13.7) | 1.243 (11.0) |
| 5 | — | 2.581 (22.8) | 3.590 (31.8) | 2.875 (25.4) |
| 7.5 | — | 3.765 (33.3) | 5.367 (47.5) | 4.874 (43.1) |
| 10 | — | 5.248 (46.4) | 6.964 (61.6) | 6.019 (53.3) |
| 20 | — | 10.906 (96.5) | 14.955 (132.4) | 10.712 (94.8) |

[1] Solubility enhancement ratio is the ratio between the drug solubility in the vehicle containing various amounts of cyclodextrins and the drug solubility in the vehicle alone
[2] Aqueous solubility of β-cyclodextrin is very poor; at 2% level, it requires heating to dissolve it completely.
[3] Cavasol W7M is a trade name for methyl-β-cyclodextrin from Wacker-Chemie GmbH.
[4] Crystalline methylated β-cyclodextrin from Pitha & Pitha, LLC. At 20% w/v concentration, it requires heating to facilitate its dissolution.

TABLE 2

Solubility of Carbamazepine in Selected Vehicles

Carbamezepine Solubility, mg/ml

| Water | Propylene Glycol | PEG 400 | Transcutol |
|---|---|---|---|
| 0.113 | 35.330 | 77.918 | 78.094 |

TABLE 3

Solubility of Fenofibrate in Selected Vehicles Containing Various Amounts of Crystalline methylated β-Cyclodextrin or Hydroxypropyl β-cyclodextrin Fenofibrate Solubility, mg/ml (solubility enhancement ratio)[1]

| Concentration, % w/v | Cryst. Methylated β-CD[2] Water | HP β-cyclodextrin Water | HP β-cyclodextrin Water:PG[3] (7:3) | HP β-cyclodextrin Water:PG (4:6) | HP β-cyclodextrin PG |
|---|---|---|---|---|---|
| 0  | 0.011     | 0.011      | 0.024      | 0.084      | 2.773      |
| 10 | 0.55 (50) | —          | —          | —          | —          |
| 16 | —         | 0.188 (17) | 0.102 (4)  | 0.272 (3)  | 3.350 (1.2)|
| 20 | 1.37 (125)| —          | —          | —          | —          |
| 28 | —         | 0.400 (36) | 0.225 (9)  | 0.448 (5)  | 3.628 (1.3)|

[1] Solubility enhancement ratio is the ratio between the drug solubility in the vehicle containing various cyclodextrins and the drug solubility in the vehicle alone.
[2] Crystalline methylated β-cyclodextrin was a gift from Pitha & Pitha, LLC. At 20% w/v concentration, it requires heating to facilitate its dissolution.
[3] PG = Propylene Glycol

TABLE 4

Solubility of Oxcarbazepine in Aqueous Solution of Various Cyclodextrins and Tween 80

Oxcarbazepine Solubility, mg/ml (solubility enhancement ratio)[1]

| Concentration. % (w/v) | Tween 80 | Cavasol W7M[2] | Cryst. Methylated β-CD[3] | HP-β-cyclodextrin |
|---|---|---|---|---|
| 0  | 0.07       | 0.07       | 0.07       | 0.07       |
| 1  | 0.12 (1.7) | 0.15 (2.1) | 0.23 (3.3) | 0.13 (1.9) |
| 2  | 0.17 (2.4) | 0.24 (3.4) | 0.31 (4.4) | 0.19 (2.7) |
| 5  | 0.29 (4.1) | 0.49 (7.0) | 0.82 (11.7)| 0.34 (4.9) |
| 10 | 0.50 (7.1) | 0.67 (9.6) | 1.49 (21.3)| 0.67 (9.6) |

[1] Solubility enhancement ratio is the ratio between the drug solubility in the vehicle containing various amounts of Tween 80 or cyclodextrins and the drug solubility in the vehicle alone.
[2] Cavasol W7M is a trade name for methyl-β-cyclodextrin from Wacker-Chemie GmbH.
[3] Crystalline methylated β-cyclodextrin was a gift from Pitha & Pitha, LLC. At 20% w/v concentration, it requires heating to facilitate its dissolution.

TABLE 5

Solubility of Glipizide in Aqueous Solution of Various Cyclodextrins

Glipizide Solubility, mg/ml (solubility enhancement ratio)[1]

| Concentration. % (w/v) | γ-Cyclodextrin | Cavasol W7M[2] | Cryst. Methylated β-CD[3] | HP-β-cyclodextrin |
|---|---|---|---|---|
| 0  | 0.037          | 0.037           | 0.037           | 0.037          |
| 1  | 0.0244 (0.66)  | 0.049 (1.32)    | 0.1045 (2.82)   | 0.0575 (1.55)  |
| 2  | 0.0415 (1.12)  | 0.0626 (1.69)   | 0.1760 (4.76)   | 0.0727 (1.96)  |
| 5  | 0.0339 (0.92)  | 0.1740 (4.70)   | 0.3988 (10.78)  | 0.1281 (3.46)  |
| 10 | 0.0402 (1.08)  | 0.4882 (13.19)  | 0.9861 (26.65)  | 0.2294 (6.20)  |
| 15 | 0.0366 (0.99)  | 0.5607 (15.15)  | 1.5513 (41.93)  | 0.3418 (9.24)  |

[1] Solubility enhancement ratio is the ratio between the drug solubility in the aqueous vehicle containing various cyclodextrins and the drug solubility in the aqueous vehicle alone.
[2] Cavasol W7M is a trade name for methyl-β-cyclodextrin from Wacker-Chemie GmbH.
[3] Crystalline methylated β-cyclodextrin was a gift from Pitha & Pitha, LLC. At 20% w/v concentration, it requires heating to facilitate its dissolution.

What is claimed is:

1. A pharmaceutical composition, comprising a solubilizing agent selected from crystalline methylated α-, β-, and γ-cyclodextrin, or mixtures thereof, and a pharmaceutically active agent.

2. The composition of claim 1, wherein the solubilizing agent is crystalline methylated β-cyclodextrin.

3. The composition of claim 1, wherein the active agent is one that has poor aqueous solubility.

4. The composition of claim 1, which is an oral or parenteral solution.

5. The composition of claim 1, which is a liquid or cream preparation for external use.

6. The composition of claim 1, which is in the form of a solid dosage unit.

7. The composition of claim 1, which is a solid oral dosage unit.

8. The composition of claim 1, which is a tablet or capsule.

9. The composition of claim 1, which is an osmotic dosage unit.

10. The composition of claim 1, wherein the active agent is carbamazepine, fenofibrate, oxcarbazepine, or glipizide.

* * * * *